United States Patent [19]

Filippovich et al.

[11] Patent Number: 5,616,813
[45] Date of Patent: Apr. 1, 1997

[54] VINYL ETHER COMPOUND, PROCESS FOR PRODUCING THE SAME AND COPOLYMER CONTAINING THE SAME

[75] Inventors: Cherstokov V. Filippovich, Moscow; Sterlin S. Rafailovich, Moscow; S. Lev German, deceased, late of Moscow, all of Russian Federation, by Elena N. German, legal representative; Lin Jeng-Tain, Kitaibaraki, Japan; Satoru Saito; Haruyoshi Tatsu, both of Ibaraki, Japan

[73] Assignee: Nippon Mektron Limited, Tokyo, Japan

[21] Appl. No.: 551,272

[22] Filed: Oct. 31, 1995

[30] Foreign Application Priority Data

Nov. 17, 1994 [JP] Japan .................................. 6-308198
Jul. 13, 1995 [JP] Japan .................................. 7-200357

[51] Int. Cl.[6] .................................. C07C 49/76
[52] U.S. Cl. .................................. 568/663; 526/244
[58] Field of Search .................................. 568/663

[56] References Cited

PUBLICATIONS

An 1973:5154; DN 78:5154 "Terpdymers of Tetra–Fluoroethylene and Perfluoro Derivatives" Kalb et al Nuova Chim. Journal (1972), 48(9), 9L2.

Primary Examiner—Joseph L. Schofer
Assistant Examiner—N. Sarofim
Attorney, Agent, or Firm—Barnes & Thornburg

[57] ABSTRACT

A novel bifunctional vinyl ether compound having an aromatic ring, represented by the following general formula:

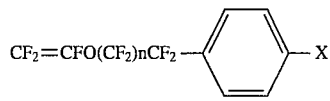

where X is a halogen atom and n is an integer of 1 to 5, effective as a copolymer component for fluorine-containing elastomers is produced by adding a chlorine atom or a bromine atom (Y) to $CF_2=CFO(CF_2)nCOOR$, where R is a lower alkyl group, then subjecting the resulting $CF_2YCFYO(CF_2)nCOOR$ to hydrolysis and acid chloridation, followed by reaction with monohalogenobenzene, reaction with $SF_4$ to convert —CO— to —$CF_2$—, and dechlorination or debromination, or by subjecting $CF_2=CFO(CF_2)nCOOR$ to hydrolysis and acid chloridation, followed by reaction with monohalogenobenzene and reaction with SF, to convert —CO— to —$CF_2$—.

1 Claim, No Drawings

VINYL ETHER COMPOUND, PROCESS FOR PRODUCING THE SAME AND COPOLYMER CONTAINING THE SAME

BACKGROUND OF THE INVENTION

1. Field of the Invention

The present invention relates to a novel vinyl ether compound, a process for producing the same and a copolymer containing the same, and more particularly to a novel vinyl ether compound as an effective copolymer component for fluorine-containing elastomers, a process for producing the same and a copolymer containing the same.

2. Related Prior Art

Fluorine-containing elastomers have now had a good reputation not only for their good heat resistance, but also for their resistance to oil and chemicals, and bifunctional vinyl ethers as a copolymer component for these fluorine-containing elastomers are now attracting keen attention.

SUMMARY OF THE INVENTION

An object of the present invention is to provide a novel bifunctional vinyl ether compound having an aromatic ring, which acts as an effective copolymer component for fluorine-containing elastomers.

Another object of the present invention is to provide a process for producing such a novel vinyl ether compound.

Other object of the present invention is to provide a fluorine-containing elastomer copolymer containing such a novel vinyl ether compound as cross-linking site for vulcanization.

DETAILED DESCRIPTION OF THE INVENTION

According to the present invention there is provided a vinyl ether compound represented by the following general formula:

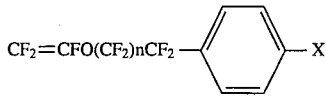

X: halogen atom
n: an integer of 1 to 5

Such a vinyl ether compound can be produced through a series of the following steps:

$$CF_2=CFO(CF_2)nCOOR \rightarrow CF_2YCFYO(CF_2)nCOOR \quad (1)$$

R: lower alkyl group
Y: chlorine or bromine atom
n: an integer of 1 to 5

This addition reaction can be readily carried out by bubbling of a chlorine gas through a lower alkyl ester compound or by dropwise addition of bromine to the lower alkyl ester compound, preferably under ultraviolet irradiation. The raw material lower alkyl ester can be produced by esterification of $CF_2=CFO(CF_2)nCOOH$ according to the conventional method, where $CF_2=CFO(CF_2)nCOOH$ can be obtained by thermal decomposition of $FOCCF(CF_2)O(CF_2)nCOOR$ in the presence of an alkali metal carbonate, which is a product from addition reaction of $FOC(CF_2)mCOOR$, where m is n-1, with hexafluoropropene oxide. The starting material $FOC(CF_2)mCOOR$ can be obtained through reaction of $FOC(CF_2)mCOF$ with ROH.

$$CF_2YCFYO(CF_2)nCOOR \rightarrow CF_2YCFYO(CF_2)nCOOH \quad (2)$$

This hydrolysis reaction can be carried out by stirring $CF_2YCFYO(CF_2)nCOOR$ together with sodium hydroxide, potassium hydroxide or the like dissolved in methanol, ethanol or the like to once isolate it as a sodium carboxylate salt, a potassium carboxylate salt or the like, and then neutralizing the salt with hydrochloric acid, sulfuric acid or the like.

$$CF_2YCFYO(CF_2)nCOOH \rightarrow CF_2YCFYO(CF_2)nCOCl \quad (3)$$

This acid chloridazation reaction can be readily carried out according to the conventional method for converting a carboxyl group to an acid chloride group, that is, with thionyl chloride in the presence of a pyridine catalyst.

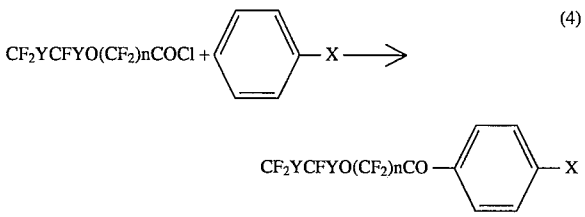

X: halogen atom

This condensation reaction can be readily carried out with monofluorobenzene, monoiodobenzene, monobromobenzene or monochlorobenzene, using aluminum chloride or the like as a catalyst.

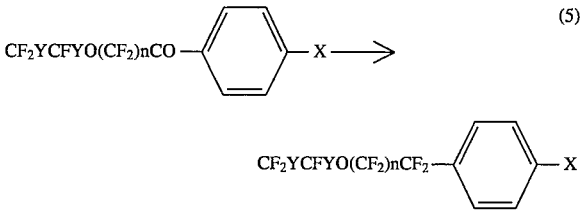

This reduction reaction is carried out in an autoclave at a temperature of about 100° to about 200° C. for about 1 to about 150 hours, using $SF_4$ as a reducing agent, where a small amount of water or anhydrous hydrofluoric acid is usually made present in the reaction system as a reaction promoter.

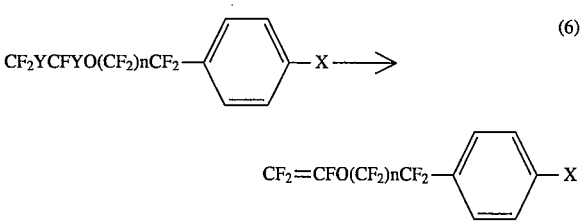

This dechlorination reaction or debromination reaction for forming a vinyl ether compound is carried out by charging powdery zinc, a solvent such as dimethyl formamide, dimethyl acetamide, methanol, ethanol or the like, and iodine as a zinc-activating agent into a reactor vessel, heating the reactor vessel to a temperature of about 20° to about 150° C. and then dropwise adding a solution containing the ether compound as dissolved therein to the reactor vessel.

The present vinyl ether compound can be also produced by a series of the following steps:

$$CF_2=CFO(CF_2)nCOOR \rightarrow CF_2=CFO(CF_2)nCOOH \quad (1')$$

This hydrolysis reaction is carried out in the same manner as in (2).

$$CF_2=CFO(CF_2)nCOOH \rightarrow CF_2=CFO(CF_2)nCOCl \quad (2')$$

This acid chloridazation reaction is carried out in the same manner as in (3).

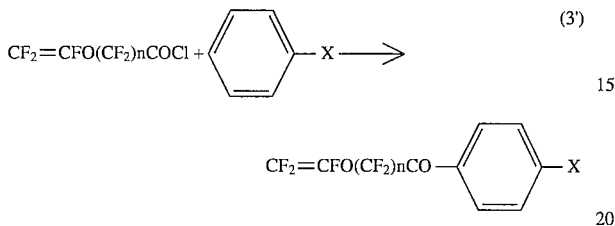

(3')

This condensation reaction is carried out in the same manner as in (4).

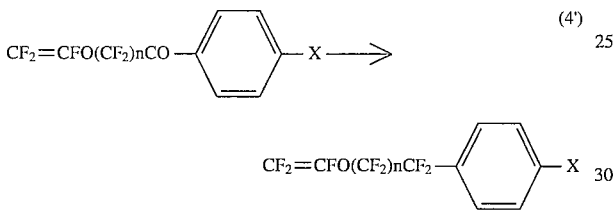

(4')

This reduction reaction is carried out in the same manner as in (5).

Novel vinyl ether compounds obtained through these series of the foregoing steps are used to form fluorine-containing elastomer copolymers through copolymerization with tetrafluoroethylene and perfluoro(lower alkyl vinyl ether) or perfluoro (lower alkoxy-lower alkyl vinyl ether).

Generally, perfluoro(methyl vinyl ether) is used as a perfluoro(lower alkyl vinyl ether) and the following ethers are used as a perfluoro(lower alkoxy-lower alkyl vinyl ether):

| | |
|---|---|
| $CF_2 = CFOCF_2CF(CF_3)CF_nF_{2n+1}$ | (n: 1–5) |
| $CF_2 = CFO(CF_2)_3OC_nF_{2n+1}$ | (n: 1–5) |
| $CF_2 = CFOCF_2CF(CF_3)O(CF_2O)_mC_nF_{2n+1}$ | (n: 1–5; m: 1–3) |
| $CF_2 = CFO(CF_2)_2OC_nF_{2n+1}$ | (n: 1–5) | where the $C_nF_{2n+1}$ group is preferably a $CF_3$ group.

Copolymerization reaction can be carried out with about 30 to about 70% by mole of tetrafluoroethylene, about 65 to about 25% by mole of perfluoro(lower alkyl vinyl ether) or perfluoro(lower alkoxy-lower alkyl vinyl ether) and about 0.1 to about 5% by mole of the present vinyl ether compound, the sum total being 100% by mole, according to any polymerization method such as emulsion polymerization method, suspension polymerization method, solution polymerization method, bulk polymerization method, etc., where the emulsion polymerization method is preferable from the economical viewpoint.

Emulsion polymerization reaction can be carried out usually at a temperature of about 40° to about 85° C. under a pressure of about 3 to 8 MPa, using a water-soluble inorganic peroxide or its redox system as a catalyst and ammonium perfluorooctanoate or the like as a surfactant. Such amounts of fluoroolefin, olefin, vinyl compounds, etc. as not to inhibit the copolymerization reaction and not to impair the vulcanization properties, for example, not more than 20% by mole on the basis of the copolymer, can be copolymerized into the terpolymer.

Vulcanization of the thus obtained fluorine-containing elastomer copolymer is carried out in the following manner:

A mixture of 100 parts by weight of the thus obtained terpolymer and about 0.5 to about 5 parts by weight, preferably about 1 to about 2 parts by weight, of an aliphatic diamine, such as hexamethylenediamine, ethylenediamine, etc., an aromatic polyfunctional compound represented by the following general formulae [where R is $CF_2$, $C(CF_2)_2$, $SO_2$ or the like throughout all the formulae]:

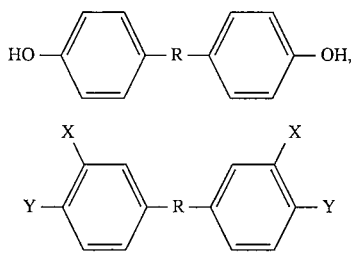

where one of Z and Y is an amino group and the other is a mercapto group,

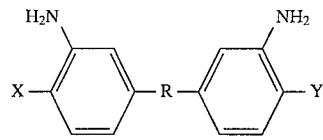

where X and Y are hydroxyl groups or amino groups, and

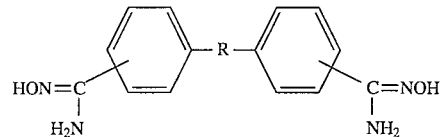

or alkali metal salt thereof is press vulcanized at a temperature of about 160° to about 250° C., followed by oven vulcanization (secondary vulcanization) when required. To enhance the vulcanization speed, it is effective to use an interphase migration catalyst such as a quaternary ammonium salt, a quaternary phosphonium salt, polyalkylene oxide, dicyclohexyl-18-Crown, etc. as a vulcanization promoter. Besides these components, carbon black as a filler and a divalent metal oxide or hydroxide as an acid receptor, etc. can be contained in the vulcanization mixture, when required.

According to the present invention a vinyl ether compound represented by the following general formula is provided:

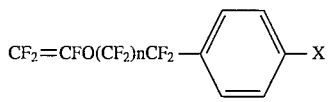

where X is a halogen atom and n is an integer of 1 to 5. This novel compound acts as cross-linking sites for vulcanization, when copolymerized into fluorine-containing elastomers.

PREFERRED EMBODIMENTS OF THE INVENTION

The present invention will be described in detail below, referring to Examples.

EXAMPLE 1

(1) 360 g of $CF_2=CFO(CF_2)_3COOCH_3$ was charged into a reactor vessel having a capacity of 500 ml, and 71 g of a chlorine gas was bubbled therethrough under irradiation of an ultraviolet lamp (PRK-2) over 15 hours. After the end of reaction, 301.7 g of $CF_2ClCFClO(CF_2)_3COOCH_3$ was obtained as a fraction having a boiling point of 75°–76° C./25 mmHg by distillation (yield: 69%).

Mass spectrum: M/e 209 $(CF_2ClCFClO)^{\oplus}$ 151 $(CF_2ClCFCl)^{\oplus}$ $^{19}F$- NMR: $CF_2ClCFClOCF_2CF_2CF_2COOCH_3$
$\phantom{xx}$ 5 $\phantom{xx}$ 4 $\phantom{xxx}$ 3 2 1

(1) 42.2 ppm
(2) 50.05 ppm
(3a) 6.2 ppm
(3b) 8.1 ppm $\phantom{xx}$ Jab = 184 Hz
(4) 0.0 ppm
(5a) –6.2 ppm
(5b) –5.2 ppm $\phantom{xx}$ Jab = 173 Hz (2) 22 g (0.4 moles) of potassium hydroxide dissolved in 60 ml of methanol was added to 66.9 g (0.18 moles) of $CF_2ClCFClO(CF_2)_3COOCH_3$ and the mixture was stirred at room temperature for one hour and then methanol was distilled off under reduced pressure. 30 ml of 50% sulfuric acid was added to the residue and then 64.4 g of $CF_2ClCFClO(CF_2)_3COOH$ was obtained as a fraction having a boiling point of 112° C./28 mmHg by distillation (yield: 88%).

Mass spectrum: M/e 195 $(ClCF_2CFClO)^{\oplus}$ 151 $(ClCF_2CFCl)^{\oplus}$ 150 $(CF_2CF_2CF_2)^{\oplus}$ 85 $(CF_2Cl)^{\oplus}$ $^{19}F$-NMR: $CF_2ClCFClOCF_2CF_2CF_2COOCH_3$
$\phantom{xx}$ 5 $\phantom{xx}$ 4 $\phantom{xxx}$ 3 2 1

(1) 42.8 ppm
(2) 50.05 ppm
(3a) 6.2 ppm
(3b) 8.2 ppm $\phantom{xx}$ Jab = 186 Hz
(4) 0.0 ppm
(5a) –6.2 ppm
(5b) –5.2 ppm $\phantom{xx}$ Jab = 172 Hz (3) 24.0 g (0.2 moles) of thionyl chloride $SOCl_2$ and 1 ml of pyridine were added to 46.0 g (0.12 moles) of $CF_2ClCFClO(CF_2)_3COOH$ and the mixture was refluxed for 8 hours. After the end of reaction, 42.6 g of $CF_2ClCFClO(CF_2)_3COCl$ was obtained as a fraction having a boiling point of 64°–65° C./32 mmHg by distillation (yield: 88%).

(4) 66 g of aluminum chloride was added to a mixture solution of 160 g (0.42 moles) of $CF_2ClCFClO(CF_2)_3COCl$ and 100 ml (1.07 moles) of monofluorobenzene, and the mixture was stirred at 35°–40° C. for 2 hours. Then, 300 g of ice was added thereto to discontinue the reaction. The organic layer of the reaction mixture was washed successively with 6N hyrdochloric acid (200 ml), water (500 ml) and a saturated aqueous sodium chloride solution (200 ml) and then 138 g of $CF_2ClCFClO(CF_2)_3CO$ (p-$C_6H_4$)F was obtained as a fraction having a boiling point of 98°–98° C./2 mmHg by distillation (yield: 74.7%).

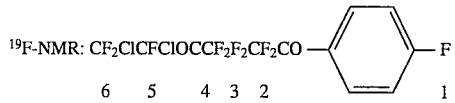

$^{19}F$-NMR: $CF_2ClCFClOCCF_2F_2CF_2CO$ —— F
$\phantom{xxxxxxxxxxxxxxxxx}$ 6 $\phantom{x}$ 5 $\phantom{xx}$ 4 3 2 $\phantom{xxx}$ 1

(1) 23.2 ppm
(2) 35.6 ppm
(3) 47.8 ppm
(4a) 5.0 ppm
(4b) 6.8 ppm $\phantom{xx}$ Jab = 144 Hz
(5) –0.7 ppm
(6a) 6.7 ppm
(6b) 6.1 ppm $\phantom{xx}$ Jab = 170 Hz (5) 135 g (0.308 moles) of $CF_2ClCFClO(CF_2)_3CO$(p-$C_6H_4$)F and 2 ml of water were poured into an autoclave having a capacity of 250 ml brought into a vacuum state, and then 110 g of $SF_4$ was poured into the autoclave. The autoclave was shaken at 155°–160° C. for 30 hours. Then, the gas was purged from the autoclave and the reaction mixture was neutralized to pH 7.0 with an aqueous sodium hydrogen carbonate solution. Then, the reaction mixture was washed with water and dried over $CaCl_2$ and 125 g of $CF_2ClCFClO(CF_2)_3CF_2$(p-$C_6H_4$)F was obtained as a fraction having a boiling point of 90° C./2 mmHg by distillation (yield: 87.7%).

(6) 23 g (1.3 moles) of powdery zinc, 100 ml of anhydrous dimethyl formamide and 0.5 g of iodine were charged into a four-necked flask having a capacity of 300 ml, provided with a stirrer, a thermometer, a reflux condenser and a dropping funnel, and the flask was heated to 110° C. Then, a solution containing 120 g (0.27 moles) of $CF_2ClCFClO(CF_2)_3CF_2$(p-$C_6H_4$)F dissolved in 30 ml of dimethyl formamide was dropwise added thereto over 20 minutes. After the dropwise addition, stirring was continued for one hour. The supernatant dimethyl formamide layer of the reaction mixture was recovered by decantation, and then the precipitates were also washed with dimethyl formamide. The supernatant dimethyl formamide solution and the resulting dimethyl formamide washing solution were joined together, and the joined solution was washed successively with dilute hydrochloric acid and with water, and dried over $CaCl_2$. 78 g of 4-(4'-fluorophenyl)-perfluoro (butyl vinyl ether) $CF_2=CFO(CF_2)_3CF_2$(p-$C_6H_4$)F was obtained as a fraction having a boiling point of 80°–82° C./32 mmHg by distillation (yield: 77%).

Purity: 98% (GLC. FS-1265, 3×3 mm)

Elemental analysis ($C_{12}H_4F_{12}O$): Found ; C 36.37%, H 1.02% Calculated; C 36.77%, H 1.80%

Mass spectrum: M/e 392 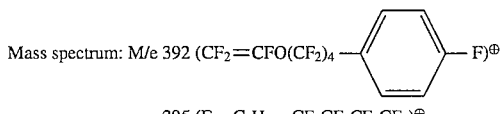

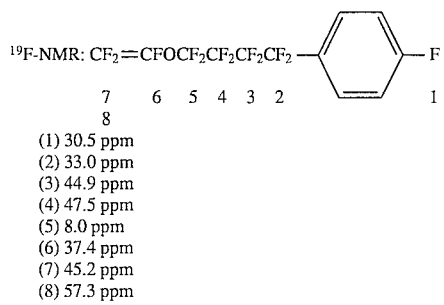

(1) 30.5 ppm
(2) 33.0 ppm
(3) 44.9 ppm
(4) 47.5 ppm
(5) 8.0 ppm
(6) 37.4 ppm
(7) 45.2 ppm
(8) 57.3 ppm

EXAMPLE 2

(1') An aqueous solution containing 40 g (0.1 mole) of sodium hydroxide dissolved in 160 ml of water was added to 306 g (0.1 mole)of methyl perfluoro(4-vinyloxybutyrate) at 0°–5° C. over 5 hours, and the mixture was returned to room temperature with stirring over 1.5 hours and then left standing for 12 hours. By distilling off water and heating the residue to dryness under reduced pressure, sodium perfluoro(4-vinyloxybutyrate) was quantitatively obtained. 100 g of the sodium salt was suspended in excess amount of concentrated sulfuric acid and the suspension was distilled under reduced pressure, whereby 91.5 g of perfluoro(4-vinyloxybutyric acid) was obtained as a fraction having a boiling point of 80°–81.5° C./20 mmHg (yield:93%).

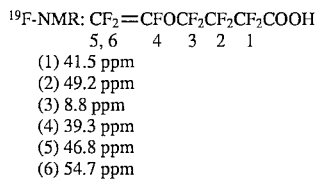

(1) 41.5 ppm
(2) 49.2 ppm
(3) 8.8 ppm
(4) 39.3 ppm
(5) 46.8 ppm
(6) 54.7 ppm (2') A mixture of 23 g of perfluoro(4-vinyloxybutyric acid), excess amount of $SOCl_2$ and 0.5 ml of pyridine was refluxed until generation of gaseous HCl was discontinued and distilled in a distillation apparatus with a Vigreaux column, whereby 24 g of perfluoro(4-vinyloxybutyric acid) chloride was obtained as a fraction having a boiling point of 97.5°–100° C. (yield: 80%).

Elemental analysis ($C_6 ClF_6O_2$): Found ; C 23.23%, F 55.49%, Cl 11.30% Calculated; C 23.23%, F 55.62%, Cl 11.63%

Infrared absorption spectrum: 1810 cm$^{-1}$ (C=O) 1840 cm$^{-1}$ (C=C)

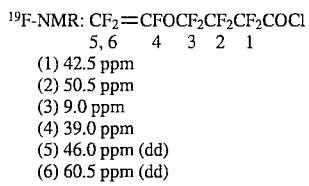

(1) 42.5 ppm
(2) 50.5 ppm
(3) 9.0 ppm
(4) 39.0 ppm
(5) 46.0 ppm (dd)
(6) 60.5 ppm (dd)

(3') 34 g (0.11 mole) of perfluoro(4-vinyloxybutyric acid) chloride was slowly added to a suspension containing 15 g (0.12 moles) of $AlCl_3$ in 100 ml of dried chlorobenzene, and the mixture was stirred at 35°–42° C. for 8 hours and then left standing overnight. Then, the reaction mixture was decomposed by dilute hydrochloric acid, and the organic layer was recovered. The aqueous layer was extracted with $CCl_4$. The recovered organic layer and the extract were joined together, and the joined mixture was washed with an aqueous dilute $NaHCO_3$ solution, dried over $MgSO_4$ and distilled, whereby 36.8 g of perfluoro (3-vinyloxypropyl)-p-chlorophenylketone was obtained as a fraction having a boiling point of 115°–116° C./10–11 mmHg (yield: 91%).

Elemental analysis ($C_{12}H_4ClF_9O_2$): Found ; C 37.34%, H 1.06%, F 43.69% Calculated; C 37.30%, H 1.03%, F 44.30%

Infrared absorption spectrum: 1500 cm$^{-1}$ (Aromatic C=C) 1600 cm$^{-1}$ (Aromatic C=C) 1720 cm$^{-1}$ (C=O) 1840 cm$^{-1}$ ($CF_2$=CF)

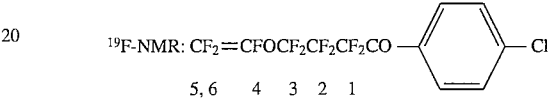

(1) 36.2 ppm
(2) 47.8 ppm
(3) 7.8 ppm
(4) 38.0 ppm
(5) 45.5 ppm
(6) 58.8 ppm (4') A mixture of 20 g (0.05 moles) of perfluoro(3-vinyloxypropyl)-p-chlorophenylktone, 10 g (0.09 moles) of $SF_4$ and 20 ml of anhydrous HF was heated in a stainless steel. autoclave at 120° C. for 15 hours, and then volatile matters were distilled off over a water bath. The residue was distilled, whereby 17.5 g of 4-(4'-chlorophenyl)-perfluoro (butyl vinyl ether) was obtained as a fraction having a boiling point of 86° C./8 mmHg (yield: 85%).

Elemental analysis ($C_{12}H_4ClF_{11}O$): Found ; C 35.45%, H 1.06%, F 51.44% Calculated; C 35.29%, H 0.98%, F 51.22%

Mass spectrum: M/e 408 [M]$^⊕$, 8 311 [M-$C_2F_3O$]$^⊕$, 100 261 ($C_9H_4F_8Cl$)$^⊕$, 17 192 ($C_8H_4F_3Cl$)$^⊕$, 53 161 ($C_7H_4F_2Cl$)$^⊕$, 55 111 ($C_6H_4Cl$)$^⊕$, 7 69 )$CF_3$)$^⊕$, 9

Infrared absorption spectrum: 1505 cm$^{-1}$ (Aromatic C=C) 1612 cm$^{-1}$ (Aromatic C=C) 1840 cm$^{-1}$ ($CF_2$=CF)

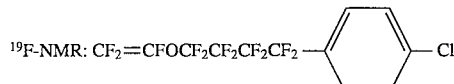

(1) 33.0 ppm
(2) 45.0 ppm
(3) 47.5 ppm
(4) 8.0 ppm
(5) 37.5 ppm
(6) 45.3 ppm
(7) 57.5 ppm

EXAMPLE 3

1.8 liters distilled water, 23.7 g of ammonium perfluorooctanoate, 14.3 g of $Na_2HPO_4.12H_2O$ and 0.67 g of $NaH_2PO_4.2H_2O$ were charged into a stainless steel autoclave having a capacity of 3 liters, and then the inside autoclave gas was replaced with a nitrogen gas, followed by pressure reduction in the autoclave. Then, 25 g of tetrafluoroethylene, 55 g of perfluoro(methyl vinyl ether) and 7.2 g of 4-(4'-fluoro -phenyl)-perfluoro(butyl vinyl ether) were successively added thereto. After the autoclave was heated to 50° C., 50 ml of an aqueous solution containing 1.66 g of sodium sulfite and 50 ml of an aqueous solution containing 9.08 g of ammonium persulfate were added thereto to initiate polymerization reaction.

During the polymerization reaction, tetrafluoroethylene, perfluoro(methyl vinyl ether) and 4-(4'-fluorophenyl)perfluoro(butyl vinyl ether) were supplementarily added to the autoclave at flow rates of 12.8 g/hr, 6.5 g/hr and 2.2 g/hr, respectively, to keep the autoclave inside pressure at 9 kg/cm$^2$ gage.

19 hours after the initiation of polymerization reaction, the supplementary addition was discontinued, and the autoclave was left standing in that state for one hour. Then, the autoclave was cooled and the remaining gas was purged therefrom. An aqueous latex having a solid content of 20% by weight was taken out of the autoclave.

The thus obtained aqueous latex was added to 20 liters of a saturated sodium chloride solution at 70° C. to coagulate the formed polymer. The coagulates were recovered by filtration, washed with water and dried at 70° C. under the atmospheric pressure for 12 hours and then dried at 120° C. under reduced pressure for 12 hours, whereby 560 g of white rubbery terpolymer was obtained. Infrared absorption spectrum revealed absorption at 1520 cm$^{-1}$ and 1615 cm$^{-1}$, confirming that perfluoro -[4-(4'-fluorophenyl)butyl vinyl ether] was copolymerized into the terpolymer.

| Terpolymer composition determined by $^{19}$F-NMR: | |
|---|---|
| Tetrafluoroethylene | 63.2% by mole |
| Perfluoro(methyl vinyl ether) | 35.3% by mole |
| 4-(4'-fluorophenyl)-perfluoro(butyl vinyl ether) | 1.5% by mole |
| Redufced viscosity $\eta$sp/c [measured at 35° C. for a 1 wt. % solution of perfluoro(2-butyl-tetrahydrofuran)]: | 1.86 ml/g |

(a) 100 parts by weight of the thus obtained terpolymer was admixed with 20 parts by weight of MT carbon black, 5 parts by weight of bisphenol AF·dipotassium salt and 4 parts by weight of dicychlohexyl-18-Crown-6 and then the mixture was kneaded through a double roll rubber mill. Torque of the kneaded product was measured at 180° C. for 30 minutes by Curastometer (trademark of a product made by Orientex K. K., Japan), and an increase in the vulcanization torque was observed. It was confirmed that the vulcanization was in progress.

The kneaded product having the above-mentioned composition was subjected to press vulcanization (primary vulcanization) at 180° C. for 30 minutes and then to oven vulcanization (secondary vulcanization) in a nitrogen gas atmosphere under the following conditions:

At 90° C. for 4 hours, Temperature elevation from 90° C. to 204° C. over 6 hours, At 204° C. for 18 hours, Temperature elevation from 204° C. to 288° C. over 6 hours, and At 288° C. for 18 hours.

Compression set of the thus obtained vulcanization product was measured and found to be 43% at 200° C. and 47% at 250° C.

(b) 100 parts by weight of the terpolymer was admixed with 20 parts by weight of MT carbon black, 3 parts by weight of bisphenol AF·dipotassium salt, 1 parts by weight of benzyltriphenylphosphonium chloride and 4 parts by weight of magnesium oxide, and then the mixture was kneaded through a double roll rubber mill. The thus obtained kneaded product was vulcanized in the same manner as in (a), and the compression set of the vulcanized product was measured and found to be 59% at 200° C. and 61% at 250° C.

(c) 100 parts by weight of the terpolymer was admixed with 20 parts by weight of MT carbon black, 3 parts by weight of bisphenol AF·dipotassium salt, 1 parts by weight of benzyltriphenylphosphonium chloride and 4 parts by weight of magnesium oxide, and the mixture was kneaded through a double roll rubber mill. The thus obtained kneaded product was vulcanized in the same manner as in (a), and the compression set of the vulcanized product was measured and found to be 66% at 200° C. and 68% at 250° C.

EXAMPLE 4

1.7 liters of distilled water, 54.6 g of ammonium perfluorooctanoate and 23.7 g of $KH_2PO_4 \cdot 2H_2O$ were charged into a stainless steel autoclave having a capacity of 3 liters, and then the inside autoclave gas was replaced with a nitrogen gas, followed by pressure reduction in the-autoclave. Then, 31 g of tetrafluoroethylene, 45 g of perfluoro(methyl vinyl ether) and 5.6 g of 4-(4'-chlorophenyl)-perfluoro(butyl vinyl ether) were successively added thereto. After the autoclave was heated to 60° C., 50 ml of an aqueous solution containing 0.18 g of sodium sulfite and 50 ml of an aqueous solution containing 1.0 g of ammonium persulfite were added thereto to initiate polymerization reaction.

During the polymerization reaction, tetrafluoroethylene, perfluoro(methyl vinyl ether) and 4-(4'-chlorophenyl)perfluoro(butyl vinyl ether) were supplementarily supplied into the autoclave at flow rates of 9.6 g/hr, 9.6 g/hr and 0.94 g/hr, respectively, to keep the autoclave inside pressure at 9 kg/cm$^2$ gage.

5 hours and 6 minutes after the polymerization initiation, the supplementary supply was discontinued and the autoclave was left standing in that state for one hour. Then, the autoclave was cooled and the remaining gas was purged therefrom. Aqueous latex having a solid content of 10.6% by weight was taken out from the autoclave.

The thus obtained aqueous latex was added to 20 liters of a saturated aqueous sodium chloride solution at 70° C. to coagulate the formed polymer. The coagulates were recovered by filtration, washed with water and dried at 70° C. under the atmospheric pressure for 12 hours and then dried at 120° C. under reduced pressure for 12 hours, whereby 125 g of white rubbery terpolymer was obtained. Infrared absorption spectrum revealed absorption at 1490 cm$^{-1}$ and 1600 cm$^{-1}$, confirming that 4-(4'-chlorophenyl)-perfluoro(butyl vinyl ether) was copolymerized into the terpolymer.

| Terpolymer composition determined by $^{19}$F-NMR: | |
|---|---|
| Tetrafluoroethylene | 72.8% by mole |
| Perfluoro(methyl vinyl ether) | 25.7% by mole |
| 4-(4'-chlorophenyl)-perfluoro(butyl vinyl ether) | 1.5% by mole |

(a) 100 parts by weight of the terpolymer was admixed with 20 parts by weight of MT carbon black, 5 parts by weight of bisphenol AF·dipotassium salt and 4 parts by weight of dicychlohexyl-18-Crown-6, and the mixture was kneaded through a double roll rubber mill. Torque of the kneaded product was measured at 180° C. for 30 minutes by Curastometer (trademark of a product made by Orientex K. K., Japan), and an increase in the vulcanization torque was observed. It was confirmed that the vulcanization was in progress.

The kneaded product having the above-mentioned composition was subjected to vulcanization under the same conditions as in Example 3 (a), and the compression set of the thus obtained vulcanization product was measured and found to be 38% at 200° C. and 41% at 250° C.

(b) The terpolymer was subjected to preparation of a kneaded product and its vulcanization in the same manner as in Example 3 (b) and the compression set of the thus obtained vulcanized product was measured and found to be 42% at 200° C. and 45% at 250° C.

(c) The terpolymer was subjected to preparation of a kneaded product and its vulcanization in the same manner as in Example 3 (c) and the compression set of the thus obtained vulcanized product was measured and found to be 48% at 200° C. and 57% at 250° C.

What is claimed is:

1. A vinyl ether compound represented by the following general formula:

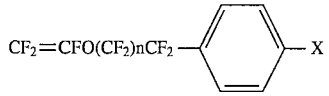

where X is a halogen atom and n is an integer of 1 to 5.

* * * * *